US005811813A

United States Patent [19]
Maor

[11] Patent Number: 5,811,813
[45] Date of Patent: Sep. 22, 1998

[54] DUAL DETECTOR GAMMA CAMERA SYSTEM

[75] Inventor: Dov Maor, Haifa, Israel

[73] Assignee: Elscint Ltd., Haifa, Israel

[21] Appl. No.: 638,713

[22] Filed: Apr. 29, 1996

Related U.S. Application Data

[63] Continuation of Ser. No. 998,771, Dec. 29, 1992, which is a continuation of Ser. No. 755,649, Sep. 6, 1991, abandoned.

[30] Foreign Application Priority Data

Dec. 6, 1990 [IL] Israel .......................................... 96578

[51] Int. Cl.$^6$ ..................................................... G01T 1/164
[52] U.S. Cl. ................................ 250/363.05; 250/363.04
[58] Field of Search ........................ 250/363.04, 363.05, 250/363.08

[56] References Cited

U.S. PATENT DOCUMENTS

| | | |
|---|---|---|
| H12 | 1/1986 | Bennett et al. ..................... 250/363.04 |
| Re. 29,216 | 5/1977 | Colombo . |
| 3,011,057 | 11/1961 | Anger ..................................... 250/204 |
| 3,549,885 | 12/1970 | Andersson . |
| 3,617,749 | 11/1971 | Massiot . |
| 3,735,132 | 5/1973 | Carugati et al. . |
| 3,756,549 | 9/1973 | Lange . |
| 3,852,601 | 12/1974 | Casale . |
| 3,870,886 | 3/1975 | Casale . |
| 3,976,885 | 8/1976 | Brunett et al. . |
| 4,049,966 | 9/1977 | Liutwieler, Jr. . |
| 4,057,727 | 11/1977 | Muehllehner et al. . |
| 4,064,441 | 12/1977 | Casale . |
| 4,216,381 | 8/1980 | Lange . |

(List continued on next page.)

FOREIGN PATENT DOCUMENTS

| | | |
|---|---|---|
| 0092437 | 10/1983 | European Pat. Off. . |
| 0131660 | 1/1985 | European Pat. Off. .......... 250/363.02 |
| 0266846 | 5/1988 | European Pat. Off. . |
| 0332937 | 3/1989 | European Pat. Off. . |
| 0465952 | 1/1992 | European Pat. Off. . |
| 0532152 | 3/1993 | European Pat. Off. . |
| 3221955 | 12/1982 | Germany . |
| 3145430 | 6/1983 | Germany . |
| 59-24280 | 8/1984 | Japan ................................ 250/363.02 |
| 83984 | 4/1986 | Japan ................................ 250/363.04 |
| 207978 | 9/1986 | Japan ................................ 250/363.04 |
| 1404060 | 6/1988 | U.S.S.R. ........................... 250/363.04 |
| 1572809 | 8/1980 | United Kingdom . |
| 2120060 | 11/1983 | United Kingdom . |

OTHER PUBLICATIONS

"Performance Analysis of Three Camera Configurations for Single Photon Emission Computed Tomography", Lim et al., *IEEE Transactions on Nuclear Science*, vol. NS–27, No. 1, Feb. 1980.

A New Development in Single Gamma Transaxial Tomography Union Carbide Focused Collimator Scanner, Stoddart et al., *IEEE*, 1979.

"Effect of an Elliptical Orbit on Spect Resolution and Image Uniformity", Gottschalk et al., *Proceedings of Third World Congress of Nuclear Energy and Medicine*, Aug.–Sep. 1982.

"The Current Status of Tomographic Scanning", Kuhl, *Fundamental Problems in Scanning*, 1968.

"Cylindrical and Section Radioisotope–Scanning of the Liver and Brain", Kuhl et al.

Lim et al., "Triangular SPECT System for 3–D Total Organ Volume Imaging: Design Concept And Preliminary Imaging Results", IEEE Transactions on Nuclear Science, vol. NS–32, No. 1, Feb. 1985, pp. 741–747.

Jaszak et al, "Physical Factors Affecting Quantitative Measurements Using Camera–Based Single Photon Emission Computed Tomography (SPECT)", IEEE Transactions on Nuclear Science, vol. NS–28, No. 1, Feb. 1981, pp. 69–80.

*Primary Examiner*—David P. Porta
*Assistant Examiner*—Richard Hanig
*Attorney, Agent, or Firm*—Fenster & Company

[57] ABSTRACT

A dual headed gamma camera arrangement wherein a first head is juxtaposed to a second head to define an angle therebetween.

3 Claims, 4 Drawing Sheets

U.S. PATENT DOCUMENTS

| | | |
|---|---|---|
| 4,220,890 | 9/1980 | Beekmans . |
| 4,223,222 | 9/1980 | Gray et al. . |
| 4,298,801 | 11/1981 | Heitman et al. . |
| 4,368,389 | 1/1983 | Blum . |
| 4,400,620 | 8/1983 | Blum . |
| 4,401,890 | 8/1983 | Blum . |
| 4,417,143 | 11/1983 | Haas et al. . |
| 4,426,725 | 1/1984 | Grady . |
| 4,445,035 | 4/1984 | Ueyama . |
| 4,476,389 | 10/1984 | Ueyama . |
| 4,503,331 | 3/1985 | Kovacs, Jr. et al. . |
| 4,523,091 | 6/1985 | Persyk ............................ 250/213 VT |
| 4,590,378 | 5/1986 | Platz . |
| 4,613,122 | 9/1986 | Manabe . |
| 4,632,123 | 12/1986 | Govaert et al. ......................... 378/198 |
| 4,645,933 | 2/1987 | Gambini et al. . |
| 4,652,758 | 3/1987 | Barford . |
| 4,652,759 | 3/1987 | Platz . |
| 4,692,624 | 9/1987 | Ichihara ............................. 250/363.04 |
| 4,692,625 | 9/1987 | Hanz et al. . |
| 4,774,410 | 9/1988 | Hsieh .................................. 250/363.1 |
| 4,888,486 | 12/1989 | Plummer et al. .................. 250/363.04 |
| 5,093,575 | 3/1992 | Perusek . |
| 5,105,086 | 4/1992 | Pierfitte et al. . |
| 5,107,121 | 4/1992 | Lim et al. .......................... 250/363.05 |
| 5,206,512 | 4/1993 | Iwao .................................. 250/363.05 |

DUAL DETECTOR GAMMA CAMERA SYSTEM

This application is a continuation, of application No. 07/998,771, filed Dec. 29, 1992, pending, which is a continuation of application No. 07/755,649, filed Sep. 6, 1991, now abandoned.

FIELD OF THE INVENTION

This invention is concerned with gamma camera systems and more particularly, with such systems using dual detector cameras.

BACKGROUND OF THE INVENTION

The original gamma camera systems used one detector head. Originally, the one detector head was positioned above an organ to be imaged. Subsequently, the one detector head was used for what is known as single photon emission computerized tomography (SPECT) or emission computerized tomography (ECT). SPECT or ECT involve mounting the camera detector head in a gantry enabling it to rotate or orbit about the patient so as to obtain tomographic data and thereby provide tomographic images. Another aspect in the development of the gamma cameras is whole body imaging wherein the gamma camera head is passed over the entire body to obtain a complete image of the patient.

To increase the efficiency of the whole body scans and the tomographic scans, multi-headed cameras have been used. First, dual-headed cameras were used wherein the gamma camera system comprised a pair of camera heads spaced apart and oppositely disposed to enable obtaining images from opposite sides of the patient simultaneously. For example, the dual heads were moved around the patient with one head on each side of the patient.

Recently triple-headed gamma camera systems have been used. In triple-headed gamma camera systems, the heads are mounted to form a triangular shape with the three planes of the heads each separated by 60°.

It would seem that multi-headed cameras would reduce the rotational travel required to obtain imaging data from a 180° orbit or a 360° orbit. It is true that with two oppositely disposed heads, the 360° orbital data can be obtained with a 180° rotation. However, the 180° orbital data cannot be obtained in a scan of 90°. Similarly, with a three-headed camera system, a 360° scan can be accomplished with an orbital movement of a little over 120°. The 180° orbital data, however, also requires a scan of 120°. From scan travel distances required it is seen that the 360° scan times are drastically reduced by multi-head systems. However, when 180° scans are required such as for cardiac studies, there is little or no time saving when using multi-headed cameras. Accordingly, a more efficient camera system is required for cardiac studies.

Another problem with the presently available gamma camera systems is in obtaining images during cardiac exercise studies. In these studies a static image is acquired while the patient pedals on an ergometer, for example. If a single camera head is used for data acquisition during the exercise study, it is oriented in an optimal left anterior oblique position. However, the behavior of the inferior wall of the heart which is of great interest to cardiologists cannot be seen from this orientation. Accordingly, a camera system is required wherein the image of the heart during exercise also includes a good view of the inferior wall of the heart.

Thus, what the present cameras do not provide is a two-headed gamma camera system with the heads oriented relative to each other to enable cardiac ECT studies in a reduced scan time. The arrangement of the two heads in the gamma camera system should assure that there is no minimum radius of rotation. The three-headed systems presently available inherently have a minimum radius of rotation which interferes with some studies, such as in pediatric applications.

Also presently lacking are gamma camera systems that can efficiently image during exercise studies and obtain images of the heart including the inferior wall. The gamma camera system that overcomes the above noted deficiencies should also provide increased count rates to enhance first pass studies.

BRIEF DESCRIPTION OF THE INVENTION

In accordance with one preferred aspect of the present invention a gamma camera system is provided having two detectors, where the detectors include a scintillating crystal, light detecting means, such as photomultipliers hereinafter often referred to as "transducer means" or "camera head"; thus, the detector comprises a crystal and photomultipliers for converting scintillations to voltages. The heads are mounted so as to describe an angular shape such as a modified L-shape wherein both legs of the "L" may be of equal size, for example. This type of camera is ideally suited for 180° ECT cardiac studies. The orientation of the two heads enables data acquisition from a 180° arc with a 90° rotational movement. This type of camera is also ideally suited for spot cardiac studies during an exercise mode. Thus, the two detectors arranged in an L-shape are mounted so that the complete heart including the inferior wall can be imaged during the exercise program.

In a broad aspect of the present invention, a unique two-headed gamma camera system for converting gamma radiation emitted from a patient to imaging data is provided, said system comprising:

means for displaying an image based on said imaging data, said dual detector camera system having a first detector and a second detector, means for mounting said second detector juxtaposed to said first detector to define an angle therebetween, and means for utilizing the camera to obtain image data.

It is a feature of the invention that a scan is obtainable by orbiting the heads about the patient for 90° which gives the equivalent of a 180° scan in effectively one-half the time.

Another feature of the present invention, utilizes a single L-shaped collimator to which the two heads are attached.

According to still another feature of the present invention, the cameras system comprises two detectors mounted with a 90° angle therebetween in a single camera.

According to yet another feature of the present invention, the gamma camera detector heads are rectangularly shaped and one side of the rectangle of each of the heads are juxtaposed to each other to form a modified L-shaped camera system. A criterion of the junction being to obtain the shortest possible patient-detector distance for both detectors. This is accomplished by arranging the inner sides of the fields of view to coincide with or be very close to the line of intersection of the detector planes.

BRIEF DESCRIPTION OF THE DRAWINGS

The above named and other features and objects of the present invention will be best understood when considered in the light of the following description of a preferred embodiment of the invention taken in conjunction with the accompanying drawings wherein.

GENERAL DESCRIPTION

Figure 1:
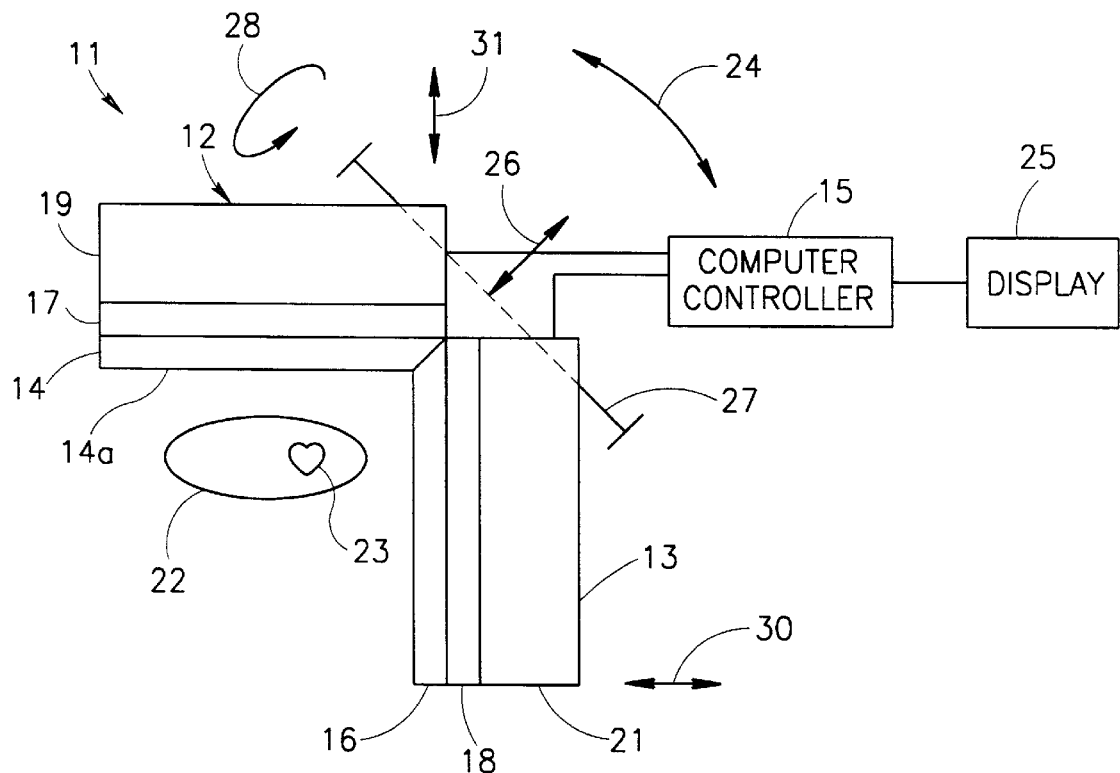
FIG. 1 is a side view of a preferred embodiment of the unique dual-headed camera arranged in a modified L-shape.

FIG. 1 shows a modified L-shaped gamma camera at 11 comprised of two gamma cameras 12 and 13. The L-shaped gamma camera arrangement is ideally suited for cardiac imaging. The gamma camera arrangement of FIG. 1 includes a collimator on each of the cameras, such as collimator 14 on camera 12 and collimator 16 on camera 13. Collimators 14 and 16 could be replaced by a single L-shaped collimator 14a. This is indicated by the dashed line at the junction of collimators 14, 16 in FIG. 1. Each of the cameras includes a crystal, which scintillates responsive to gamma radiation, such as crystal 17 on camera 12 and crystal 18 on camera 13. Behind the crystals, shown only as a block, is the transducer head 19 and 21 for cameras 12 and 13 respectively, comprised of photomultiplier tubes and electronic computer components for determining the locations of the events; i.e., the point of impact of the radiation and the crystal. The cameras acquire count, location and energy data -that are supplied to the control processor 15. The control processor processes the acquired data to provide imaging data to display unit 25.

The cameras are well known in the art. See for example, U.S. Pat. No. 3,011,057 issued to Anger. The utilization of the Anger camera in computer tomography of a single photon emission is described, for example, in IEEE Transactions on Nuclear Science, Vol. NS-23, Feb. 1976, pp. 528–537 and IEEE Transactions on Nuclear Science, Vol. NS-28, Feb. 1981, pp. 69–80.

In FIG. 1, the camera 12 is shown as being positioned immediately above the patient 22. The patient is being viewed from his feet side as is readily discernable by the location of the heart 23. The gamma camera system has the capability of orbiting the cameras about the patient as indicated by arrow 24. The system also has the capability of moving the cameras towards the patient or outward away from the patient as indicated by arrow 26. In addition, the system has the capability of swivelling the L-shaped attached cameras about an axis 27, as indicated by arrow 28. Further, the system has the ability to move the L-shaped assembly horizontally or vertically as indicated by the arrows 30 and 31 respectively. The ability to move the L-shaped assembly horizontally or vertically enables moving one of the heads closer to the patient while the other head is on a line whose distance to the patient doesn't change.

The control of the gamma camera unit to describe the motions indicated is well known to those skilled in the art. See, for example, U.S. Pat. No. 4,888,486 which shows an example of the rotational and in and out motion, and U.S. Pat. No. 4,523,091 which shows, an example of a swivel motion.

Figure 2:
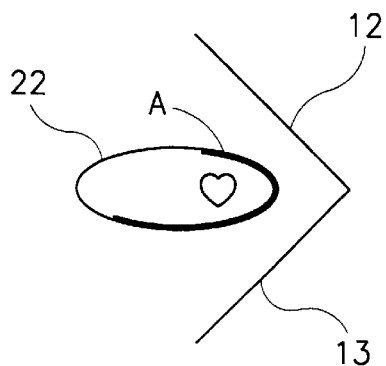
FIG. 2 in conjunction with FIG. 1, schematically shows the unique L-shaped gamma camera utilized to obtain cardiac ECT imaging data.

Cardiological procedures constitute a large fraction of the nuclear medicine clinical workload especially for ECT clinical procedure. Until now, no gamma or nuclear camera system exists which is optimized for cardiological studies. The camera system described herein is ideally suited for cardiological studies in general and for cardiac ECT studies as shown in FIG. 1 and 2. At the initiation of the study, the camera arrangement 11, for example, is in the position shown in FIG. 2 and revolves or rotates as indicated by the arrow 24 through 90° where the camera 13 is below the patient and the camera 12 is on the left side of the patient.

For example, the cameras are rectangular cameras and the connection between the two cameras is along a side of the rectangle. The camera in moving the 90° from the position of FIG. 2 performs a 180° cardiac ECT imaging acquisition. The 180° coverage is indicated by darkened section "A" of the patient in FIG. 2. The 180° cardiac ECT is performed in half the time required for a single-headed camera since it obtains 180° worth of data by a 90° rotation. Also, all of the data is obtained by cameras that are relatively close to the heart. No system on the market offers this feature.

Figure 6:
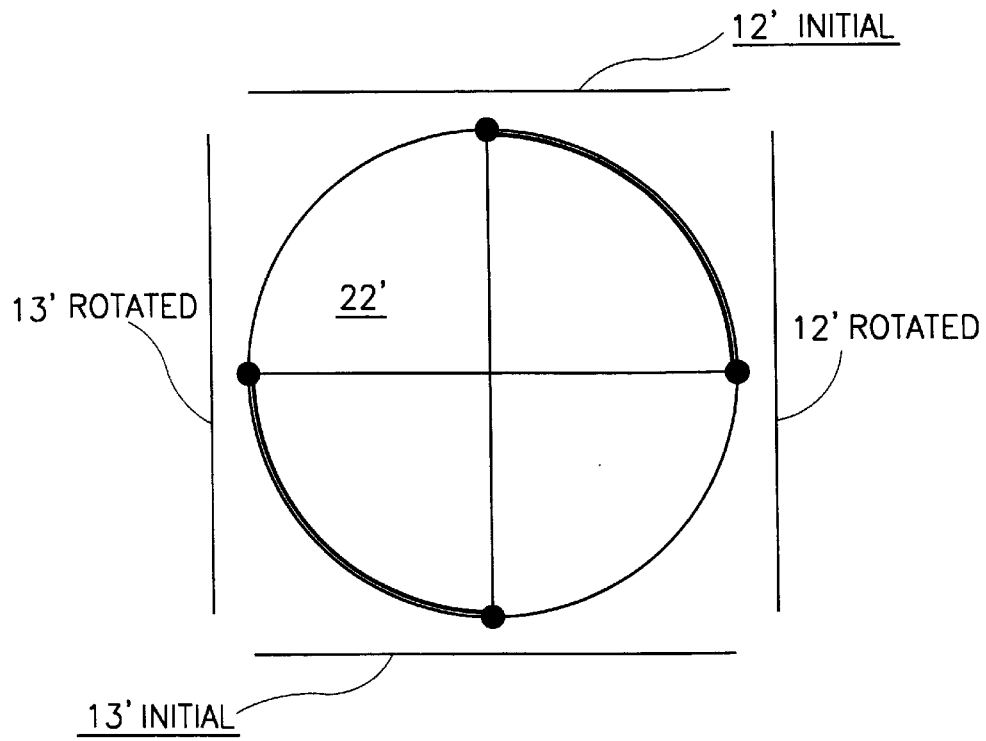
FIG. 6 schematically illustrates a shortcoming of the prior art dual-headed camera when used to acquire data in a 180° ECT scan such as used for cardiac studies.

FIG. 6 shows a prior art dual-headed camera operated to perform a 180° ECT scan. Therein the two heads 12' and 13' are spaced apart and oppositely disposed with the patient 22' therebetween. By way of example, the initial position of the oppositely disposed heads are above and below the patient and are labelled "initial". Moving the heads through 90° to the "rotated" positions provides data from separated 90° sections of the patient. Thus, insufficient data is provided for a 180° scan and further rotation and acquisition is required.

The camera arrangement 11 besides obtaining SPECT studies of the heart is also ideally suited for static cardiac imaging in any patient position. Thus, the imaging can occur while the patient is sitting on and operating an exercise cycle or ergometer. With the patient mounted on the cycle without any movement of the cameras two meaningful views are obtainable; i.e., the left anterior oblique and the left posterior oblique or the left anterior oblique and the right anterior oblique at the same time, which is especially important for dynamic studies.

Figure 3:
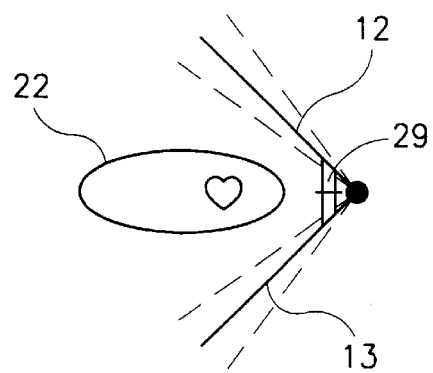
FIG. 3 shows the unique modified L-shaped gamma camera used for acquiring data during a cardiac exercise study.

A position of the camera relative to the patient in such exercise cardiac studies is illustrated in FIG. 3. Therein, the camera 12 is shown in position at the left anterior oblique position for imaging the patient 22. The camera 13 is at the left posterior oblique imaging position. Means, such as a motorized threaded member indicated at 29, may be provided for varying the angle between the cameras so that the cameras can be adjusted to have an acute angle therebetween or an obtuse angle therebetween or a right angle therebetween.

Thus, with the camera system described herein it is possible to obtain cardiological images during exercise. In these images, the static image of the heart is acquired while the patient is pedalling on an ergometer. The camera is oriented to the left anterior oblique angle which gives the best view of the heart. In prior art cameras at this angle, the behavior of the inferior wall was not visible. With the present camera system the inferior wall is clearly imaged by the second camera along with the rest of the heart.

Figure 4:
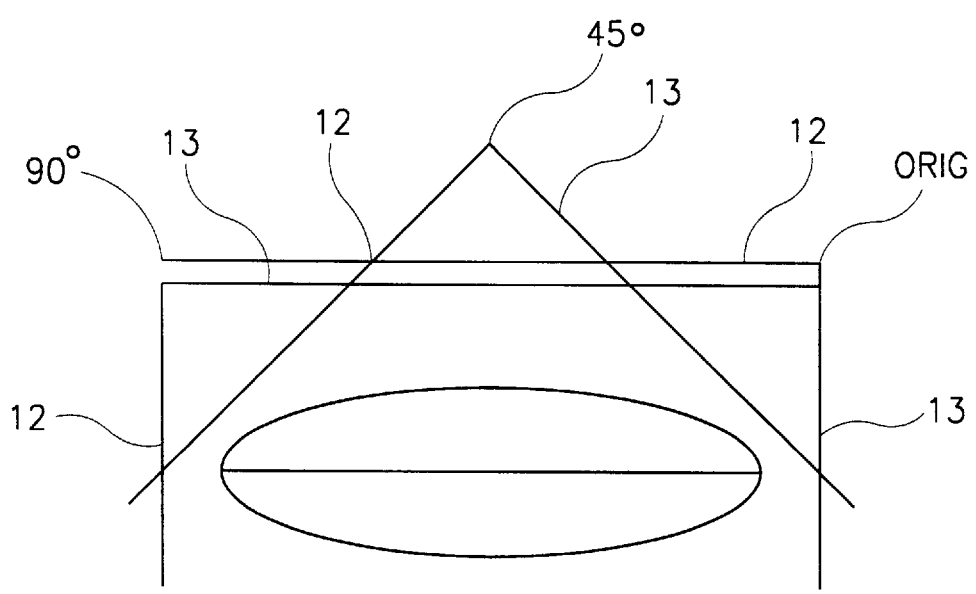
FIG. 4 schematically shows the unique modified L-shaped gamma camera utilized to obtain ECT data.

The present arrangement, as shown in FIG. 4, also makes it possible to do a 180° general SPECT with a 180° divided by two times two rotation. Thus, in FIG. 4, the camera 12 and the camera 13 are shown as being initially positioned with the camera 13 on the left side of the patient and the camera 12 above the patient. The cameras 12 and 13 are rotated through 90° from the original position indicated on FIG. 3 through many angles such as a 45° angle to the 90° angle. The 90° rotation gives a 180° SPECT data acquisition scan. Similarly, a 360° rotation enables acquiring data equivalent to a 360° scan in half the time. Using the dual cameras, almost twice the required number of counts are acquired in the normal time period or the normal number of counts are acquired in half the normal time period. The two cameras abutting each other, therefore, enable speeding up the procedure and nonetheless acquring sufficient data for tomographic images. The The camera system could also be used, of course, for a plain whole body scan. However, it is more ideally suited either for cardiological SPECT scans, cardiological exercise scans, plain SPECT scans or spot scans, including double spot scans.

Figure 5:
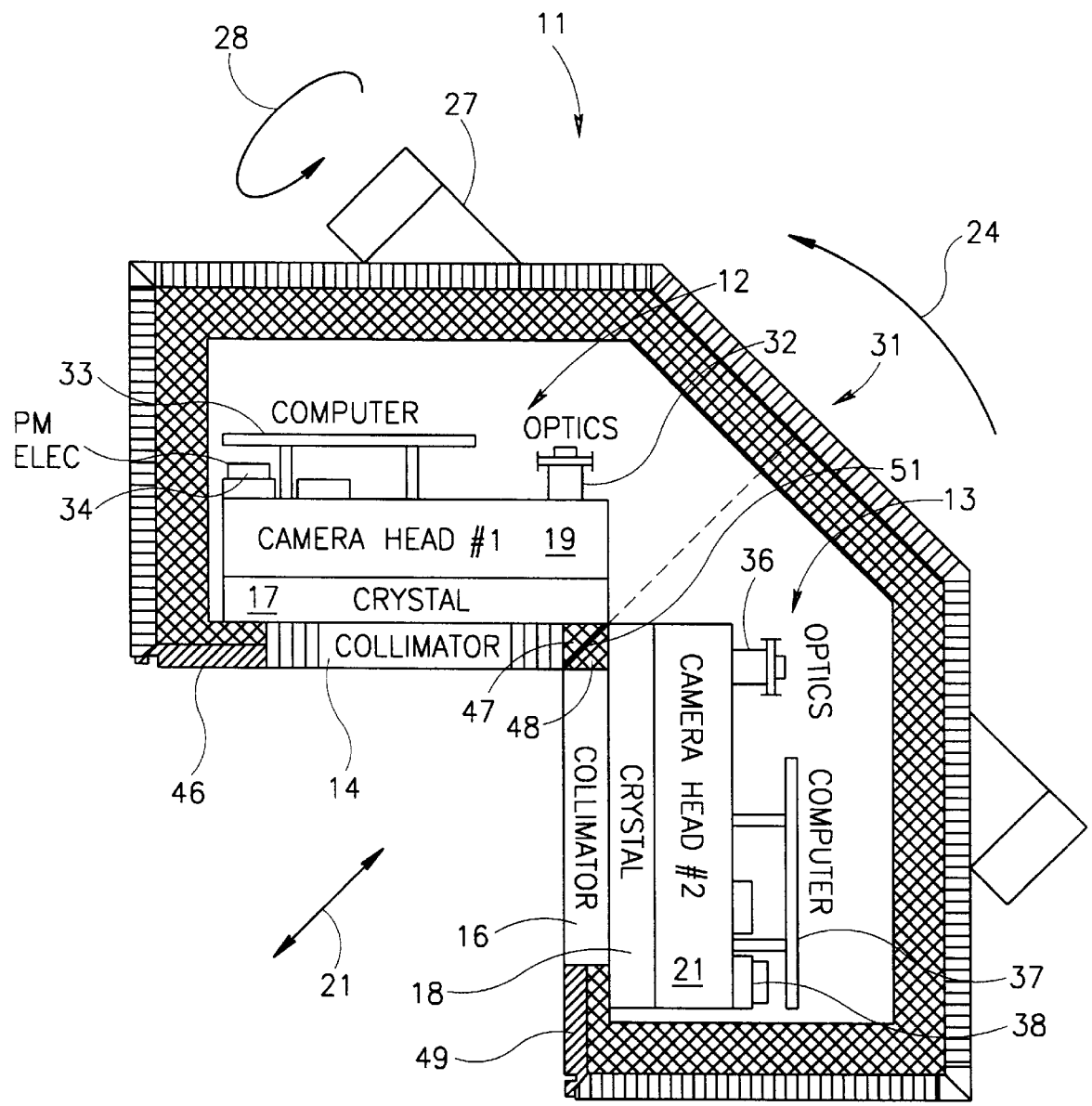
FIG. 5 shows details of one preferred embodiment of the two-detector camera head system.

FIG. 5 shows a preferred embodiment of the unique dual head camera 11. In this embodiment, the two cameras 12 and 13 are mounted in a single lead casing 31. The collimator 14, scintillator crystal 17 and transduces head or camera head 19 including camera computer 33 and the photomultiplier electronics 34 make up the camera 12. Similarly, camera 13 comprises collimator 16, scintillator crystal 18 and transduces or camera head 21 including optics 36, camera computer 37 and photomultiplier electronics 38.

Figure 7:
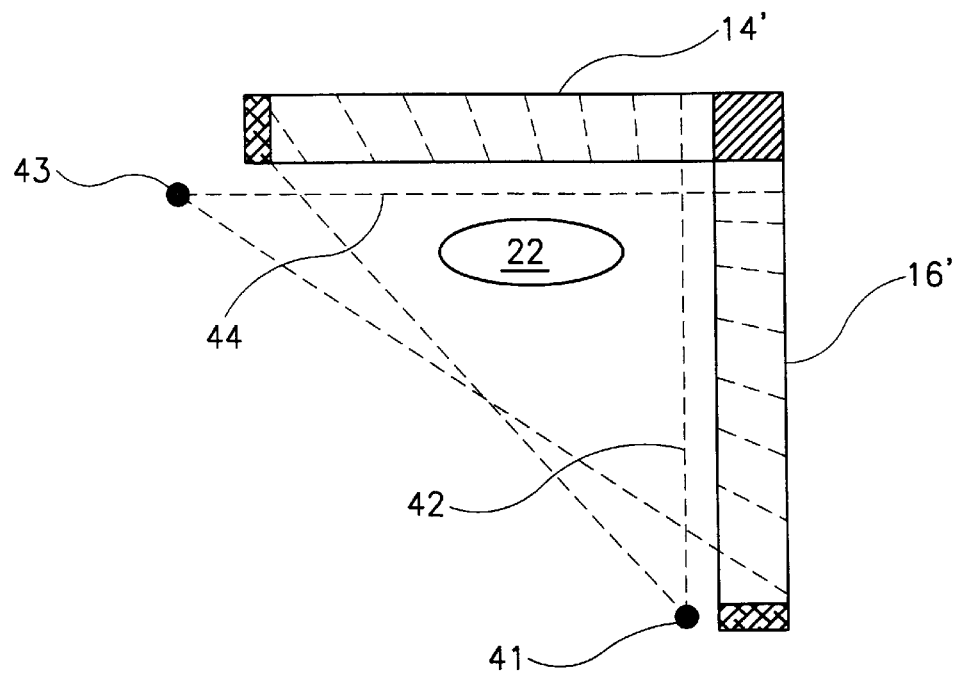
FIG. 7 shows a special fan beam collimator arrangement for the unique dual detector cameras.

In addition to normal parallel-hole collimators, special asymmetric fan-beam collimators may be provided for enabling using the system with the collimator faces as close as possible to the patient. The special collimators are shown in FIG. 7. More particularly, the collimators 14' and 16' are shown as having focal spots positioned on a straight line parallel and juxtaposed to the face of the other collimator. Thus, the slots of collimator 14' are all focused on point 41 which is located on an imaginary line 42 shown in dashed line form. The line 42 is parallel and juxtaposed to the face of collimator 16'. The slots of collimator 16' are focused on a point 43 which is located on an imaginary line parallel and Juxtaposed to the face of collimator 14'. Thus, the collimators preferably are not the usual symmetrical fan beam collimators.

The collimators 14, 16 are bordered by solid lead edges, such as edges 46, 47 for collimator 14 and edges 48, 49 for collimator 16 as shown in FIG. 5 A feature of the cameras is the means for extending the field of views (FOV) of each camera practically right up to its junction point with the other camera. Thus, the FOV of camera 12 extends to its collimator edge 47 which is practically aligned with the face of collimator 16. The edges 47 and 48 of the collimators 14 and 16 mesh at diagonal line 51 to aid in the extension of the FOVs of each camera. The line 51 could be a zig zag line to improve the radiation seal afforded by the lead casing. Alternatively, a single modified "L" shaped collimator could be used in place of collimators 14 and 16.

In practice, two rectangular gamma cameras are mounted at an angle such as 90° in a single camera head or case. The connection may be along the short side of the rectangles. The basic camera may have three degrees of freedom: rotation, in-out and swivel. The two cameras are mounted on the usual SPECT gantry which has widened arms in order to accommodate the wider camera arrangement comprising the two cameras. A preferred embodiment utilizes a single L-shaped collimator (see FIG. 1) which makes mounting of the two independent cameras to the collimators more convenient. The unique camera arrangement ideally performs 180° ECT by a 90° rotation and 360° ECT by a 360° rotation at double speed with the subsequent addition of pairs of frames taken at the same angle. Body contour and/or elliptical ECT is made possible by providing another degree of freedom either by motorizing the gantry or the bed or both for up and down and left-right movement. The described cameras are also ideally suited for imaging the heart including the inferior wall during a patient exercise procedure. It should be understood that the dual-head camera mounted at 90° can also be used for any spot imaging and provide additional data.

Thus, in summary, the advantages of the unique L-shaped camera system include the capability of performing 180° ECT with 90° of motion. In the described system, there is no minimum radius of rotation as in three-headed systems; thus, the described inventive system, is ideally suited for pediatric applications as well as cardiac studies, for example.

While the invention has been described as having a first head and a second head, the unique multi-headed camera can have more than two heads separated by angles of 90° or more.

While the invention has been described with reference to the preferred embodiment, obvious modifications and alterations will occur to those skilled in the art upon reading and understanding the preceding detailed description. It is intended that the invention be construed as including all such alterations and modifications insofar as they come within the scope of the claims or the equivalents thereof.

What is claimed is:

1. A method for simultaneously acquiring two static images of an organ in the body of a patient with the organ emitting gamma radiation while the patient is either in an upright position or lying down, said method comprising the steps of:

using gamma ray detectors consisting of only a pair of gamma ray detectors, each having a planar collimator surface for receiving incident gamma rays, with said Pair of gamma ray detectors oriented so that the planar collimator surfaces are substantially perpendicular to each other and so that both detectors of said pair of gamma ray detectors are juxtaposed to the patient to enable the simultaneous acquisition of the two images of the same organ each from different perspectives, and swivelling said pair of gamma ray detectors to selectively position said collimator surfaces at any of the positions wherein a line formed by a junction of the collimator surfaces ranges from being horizontal for acquiring said images while the patient is lying down to being vertical for acquiring said images while the patient is in an upright position.

2. The method of claim 1, further comprising moving a first detector of said pair of detectors closer to or further from the patient, while maintaining a second detector of said pair of detectors along a straight line that is at a fixed distance from the patient.

3. A gamma camera system for performing a rotational scan to form a SPECT image of an organ in the body of a patient with the organ emitting gamma radiation, said gamma camera system comprising:

a pair of gamma ray detectors, each detector having a planar collimator surface for receiving incident gamma rays; said system equipped to rotate the detectors around the patient for acquiring image data simultaneously from each of the pair of detectors at a plurality of positions during the rotation, the detectors being arranged so that the planar collimator surfaces are substantially perpendicular to each other; and means for swivelling said pair of gamma ray detectors to enable movement of said pair of gamma ray detectors from a position facing the patient while the patient is erect to a position facing the patient while the patient is lying down.

\* \* \* \* \*